(12) United States Patent
Tsuang et al.

(10) Patent No.: US 8,177,844 B2
(45) Date of Patent: May 15, 2012

(54) INSERTION APPARATUS FOR ALIGNING CAGE OF INTERVERTEBRAL FUSION

(75) Inventors: Yang-Hwei Tsuang, Taipei (TW); Cheng-Kung Cheng, Taipei (TW); Hung-Wen Wei, Taipei (TW); Chang-Jung Chiang, Taipei (TW); Ping-Sheng Yu, Taipei (TW)

(73) Assignee: National Yang-Ming University, Taipei (TW)

( * ) Notice: Subject to any disclaimer, the term of this patent is extended or adjusted under 35 U.S.C. 154(b) by 454 days.

(21) Appl. No.: 12/483,939

(22) Filed: Jun. 12, 2009

(65) Prior Publication Data

US 2010/0318028 A1 Dec. 16, 2010

(30) Foreign Application Priority Data

Feb. 24, 2009 (TW) ................................ 98105870 A

(51) Int. Cl.
*A61F 2/44* (2006.01)
*A61B 17/70* (2006.01)
(52) U.S. Cl. ................................... 623/17.11; 606/86 A
(58) Field of Classification Search .... 623/17.11–17.16; 606/86 A
See application file for complete search history.

(56) References Cited

U.S. PATENT DOCUMENTS

| 6,143,032 | A | 11/2000 | Schafer et al. |
| 6,436,119 | B1 * | 8/2002 | Erb et al. ...................... 606/198 |
| 6,648,915 | B2 | 11/2003 | Sazy |
| D533,277 | S | 12/2006 | Blain |
| 2004/0106997 | A1 | 6/2004 | Lieberson |
| 2007/0270951 | A1 * | 11/2007 | Davis et al. ................ 623/17.11 |

* cited by examiner

*Primary Examiner* — Eduardo C Robert
*Assistant Examiner* — Nicholas Plionis
(74) *Attorney, Agent, or Firm* — Muncy, Geissler, Olds & Lowe, PLLC

(57) ABSTRACT

An apparatus for inserting an intervertebral fusion cage includes a dilatation set, a guiding set and an insert set. The dilatation set includes first and second dilatation barrels non-rotationally and telescopically connected to each other. The guiding set includes first and second guiding tubes provided around the first and second dilatation barrels. The second guiding tube includes a guiding hole defined therein and a smooth arched face formed thereon in the guiding hole. The insert set includes a leading rod inserted in the second guiding tube and a push rod pivotally connected to at the leading rod. The intervertebral fusion cage is located in the second guiding tube. The fusion cage is movable out of the second guiding tube along the smooth face and the guiding hole to shorten surgery time and position the fusion cage precisely.

6 Claims, 8 Drawing Sheets

INSERTION APPARATUS FOR ALIGNING CAGE OF INTERVERTEBRAL FUSION

BACKGROUND OF THE INVENTION

1. Field of the Invention

The present invention relates to an apparatus for inserting an intervertebral fusion cage and, more particularly, to an apparatus for inserting an intervertebral fusion cage efficiently, precisely and effectively.

2. Description of the Related Art

Intervertebral disc degeneration is a common degenerative disease for senior citizens. Intervertebral disc degeneration can be treated by spinal interbody fusion with a good therapeutic effect. In the spinal interbody fusion, it is a common practice to insert a cage into the gap between two vertebral bodies to expand the gap to decompress a nerve root, relieve pain and graft intervertebral segments.

There are three approaches to the spinal interbody fusion, i.e., anterior, posterior and poster-lateral. In each approach, a specific type and amount of cages are used.

As disclosed in U.S. Patent Application Publication 2004/0106997, the poster-lateral interbody fusion is invasive to a minimal extent, keeps away from vital organs, and reduces bed-rest time. Hence, the poster-lateral interbody fusion is recommended by most medical institutes In the poster-lateral interbody fusion, only one cage is placed in the gap between the vertebral bodies. To enhance the stability, it is desirable to use a banana-shaped cage such as the one disclosed in U.S. Pat. Nos. 6,143,032, 6,648,915 and D533277.

However, since the operating angle of the poster-lateral interbody fusion with the banana-shaped cage is limited, it is difficult to place the cage between the vertebral bodies in symmetry in an anterior location. Especially, when the cage is applied through a percutaneous endoscopic route, a specially designed apparatus is required for proper localization of the cage.

SUMMARY OF THE INVENTION

It is the primary objective of the present invention to provide an apparatus for inserting an arched poster-lateral interbody fusion cage into the gap between two vertebral bodies via a percutaneous endoscope at an adjustable angle.

To achieve the foregoing objective, the apparatus includes a dilatation set, a guiding set, an insert set and an intervertebral fusion cage. The dilatation set includes two dilatation barrels. The first dilatation barrel is formed with a circular internal cross-sectional configuration and an elliptic external cross-sectional configuration. The second dilatation barrel is provided around the first dilation barrel, and includes an elliptic internal cross-sectional configuration and a circular external cross-sectional configuration. The guiding set includes two guiding tubes. The first guiding tube is provided around the second dilatation barrel. The second guiding tube is provided around the first guiding tube, and includes a radial guiding hole defined therein and a smooth face formed thereon in the guiding hole. The insert set includes a leading rod, a push rod, a tubular hammer sleeve, a block ring, a spring and a flexible element. The leading rod is inserted in the second guiding tube. The push rod is pivotally connected to the leading rod and movably inserted in the second guiding tube. The tubular hammer sleeve is connected to the leading rod. The block ring is inserted in the hammer sleeve. The spring is compressed between the block ring and the leading rod. The flexible element is connected to the block ring. The intervertebral fusion cage is connected to the flexible element, inserted in the second guiding tube, and pushed against the push rod. The flexible element includes an arced face movable out of the second guiding tube via the guiding hole along the smooth face and adjustable to a predetermined angle.

A best illustrative embodiment of the invention with drawings is described as below.

BRIEF DESCRIPTION OF THE DRAWINGS

All the objects, advantages, and novel features of the invention will become more apparent from the following detailed descriptions when taken in conjunction with the accompanying drawings wherein.

DETAILED DESCRIPTION OF THE PREFERRED EMBODIMENT

Figure 7:
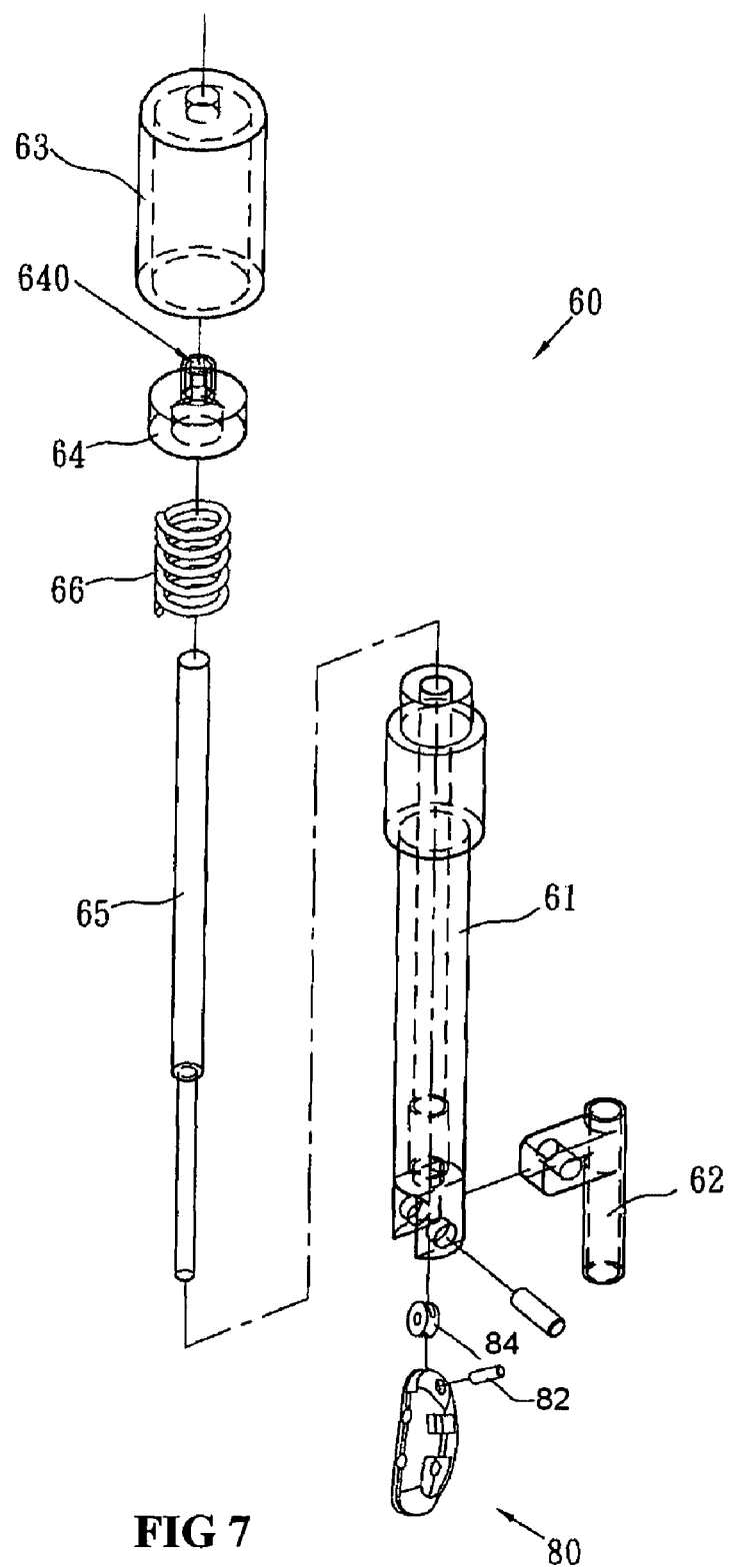
FIG. 7 is an exploded view of an insert set of the apparatus.
Figure 8:
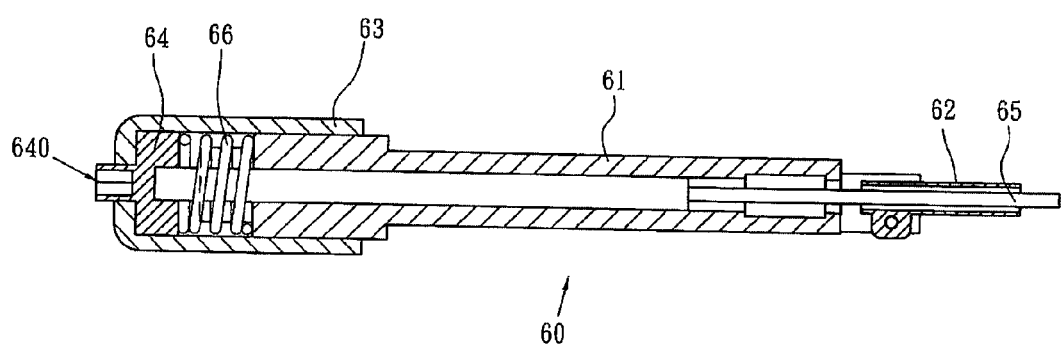
FIG. 8 is a cross-sectional view of the insert set shown in FIG. 7.
Figure 9:
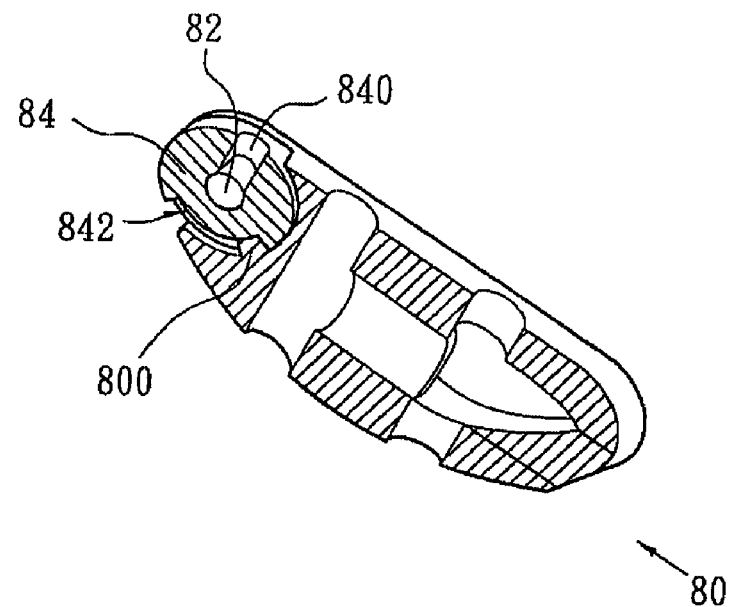
FIG. 9 is a cut-away view of an intervertebral fusion cage.
Figure 10:
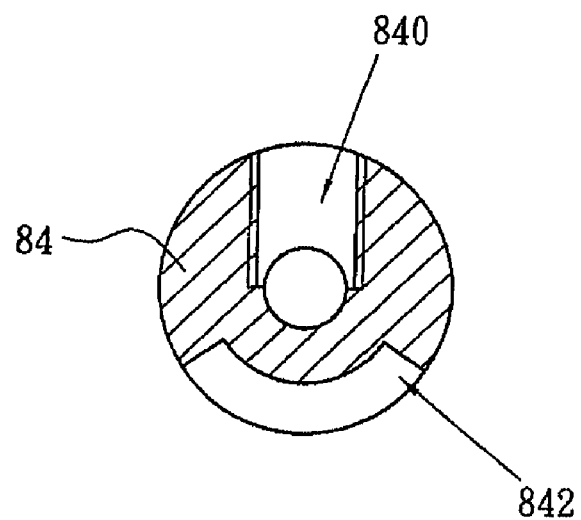
FIG. 10 is a cross-sectional view of the intervertebral fusion cage shown in FIG. 9.
Figure 11:
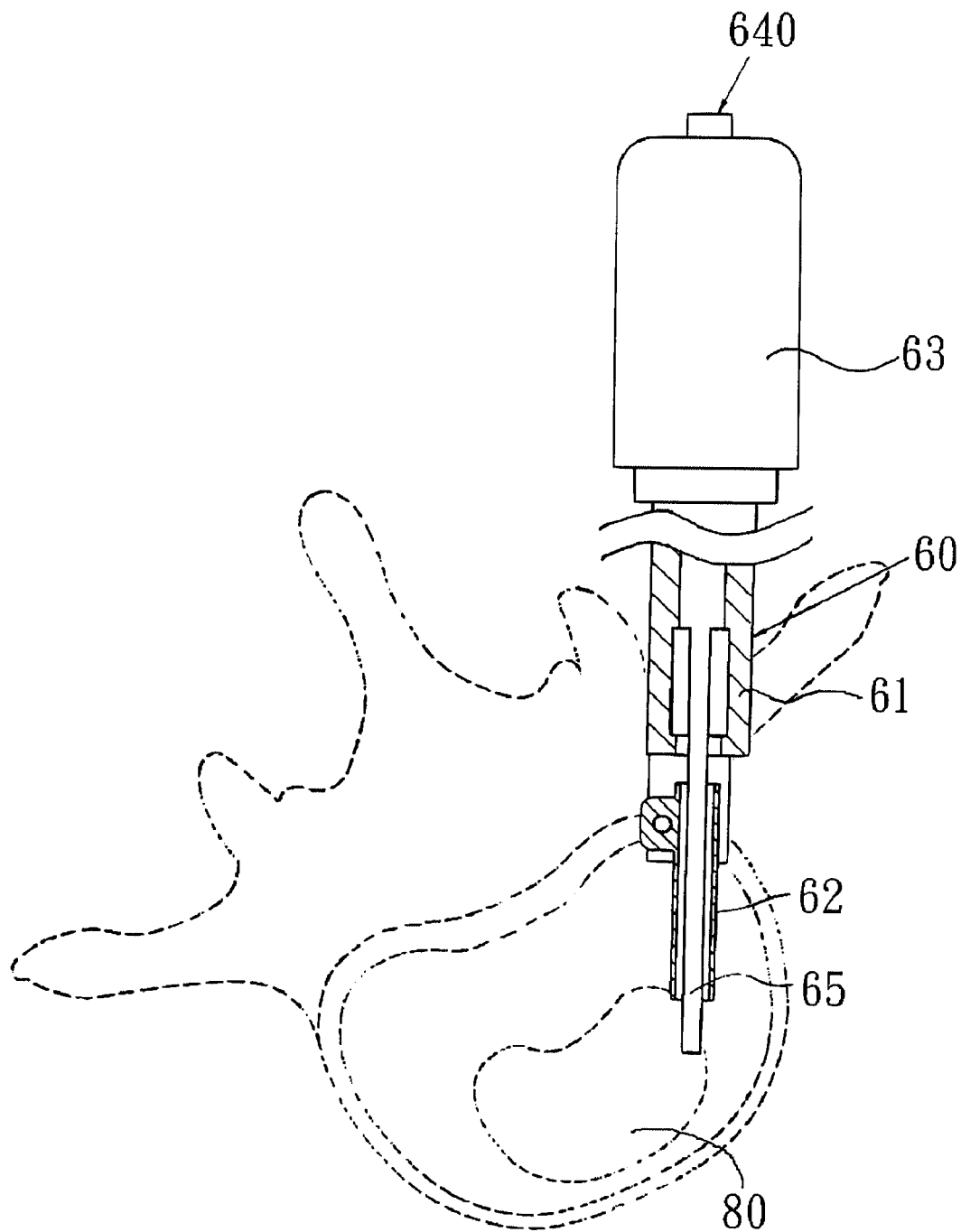
FIG. 11 is a cross-sectional view of the insert set of FIG. 7 in use.

Referring to FIGS. 1 through 8, there is shown an apparatus for inserting a cage 80 as shown in FIGS. 9 through 11 in accordance with the preferred embodiment of the present invention. The apparatus includes a dilatation set 20 for temporarily expanding the gap between two vertebral bodies, a guiding set 40 for opening a path, and an insert set 60 for inserting the cage 80 into the gap between the vertebral bodies.

Before operating the apparatus of the present invention, a patient's back is cut in a surgical method as disclosed in U.S. Patent Application Publication 2004/0106997, and a position and direction for the insertion are detected by a test rod (not shown).

Referring to FIGS. 1 to 4, the dilatation set 20 includes a first dilatation barrel 22, a second dilatation barrel 24 provided around the first dilatation barrel 22, and a handle 26 for rotating the first dilatation barrel 22. The first dilatation barrel 22 includes a circular internal cross-sectional configuration and an elliptic external cross-sectional configuration. The second dilatation barrel 24 includes an elliptic internal cross-sectional and a circular external cross-sectional configuration. The first dilatation barrel 22 is inserted through an elliptic aperture 260 defined in the handle 26. The first dilation barrel 22 can be moved but cannot be rotated relative to the handle 26 because the external cross-sectional configuration of the first dilatation barrel 22 and the aperture 260 of the handle 26 are elliptic. The first dilatation barrel 22 can be made with any other non-circular external cross-sectional configuration while the aperture 260 can be made of a corresponding non-circular form.

In use of the dilatation set 20, the first dilatation barrel 22 is inserted along the test rod so that an end of the first dilatation barrel 22 is inserted in the gap between the vertebral bodies. By rotating the handle 26 for 90 degrees, the first dilatation barrel 22 is rotated for 90 degrees. Thus, two portions of the first dilation barrel 22 at the ends of the long axis of the elliptic cross-sectional configuration of the first dilation barrel 22 are abutted against the vertebral bodies, respectively. Hence, the gap between the vertebral bodies is expanded. With the gap between the vertebral bodies expanded, the surgery is made easy, and the surgery time is rendered short. The gap between the vertebral bodies is further expanded by inserting the second dilatation barrel 24 therein along the first dilatation barrel 22.

Figure 1:
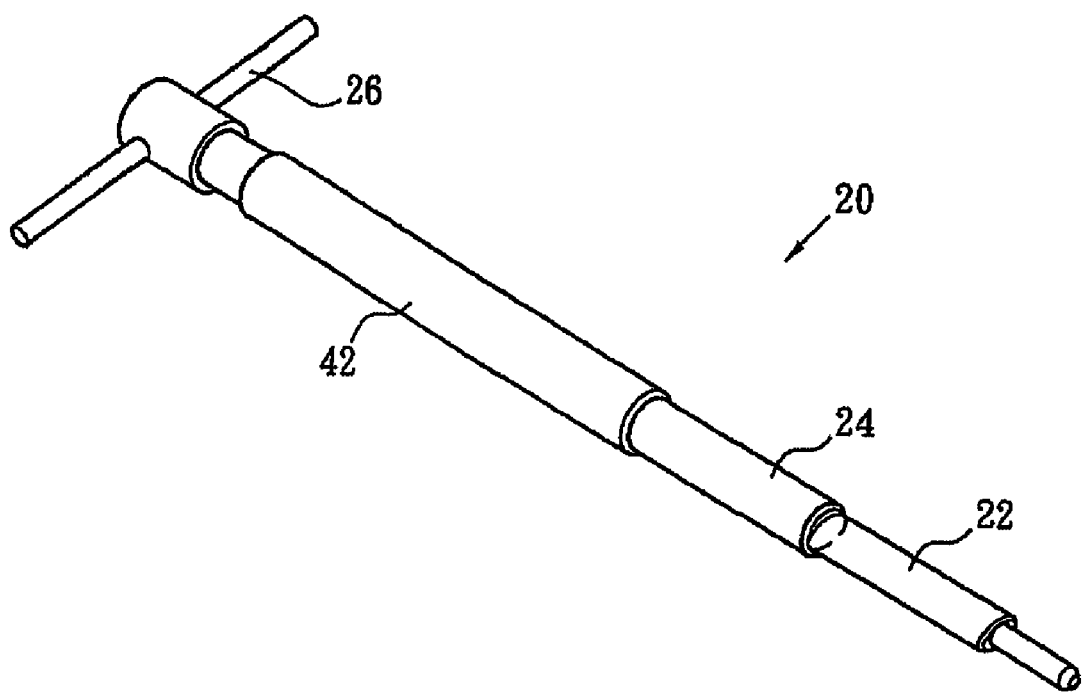
FIG. 1 is a perspective view of a dilatation set of an apparatus for inserting an intervertebral fusion cage in accordance with the preferred embodiment of the invention.
Figure 2:
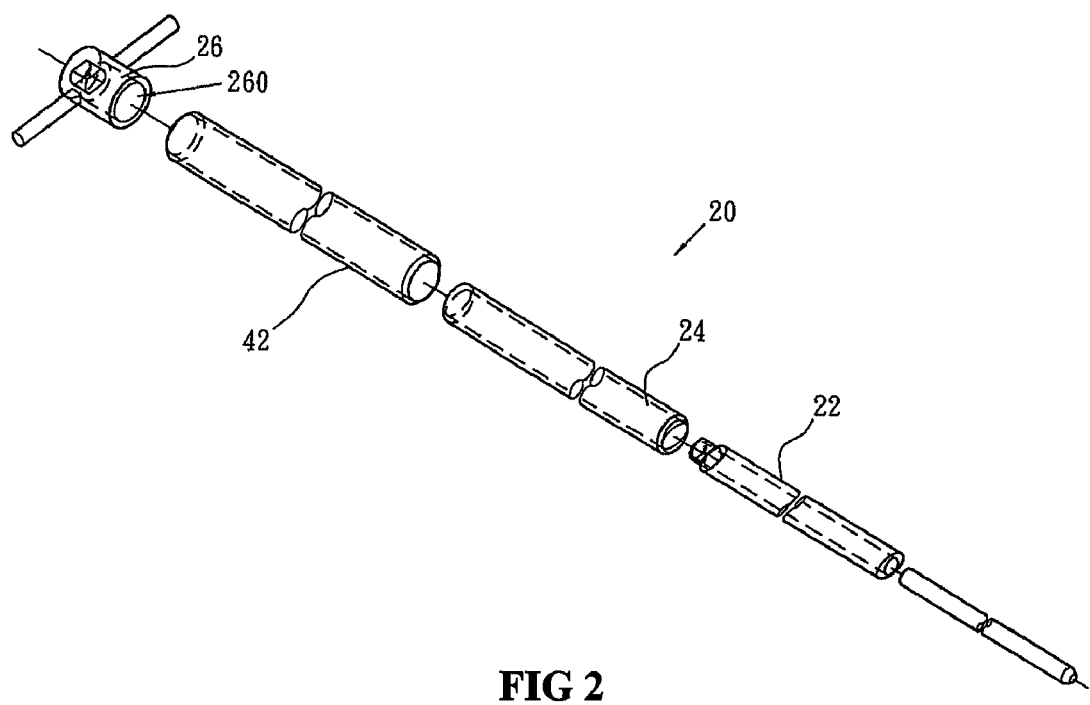
FIG. 2 is an exploded view of the dilatation set shown in FIG. 1.
Figure 3:
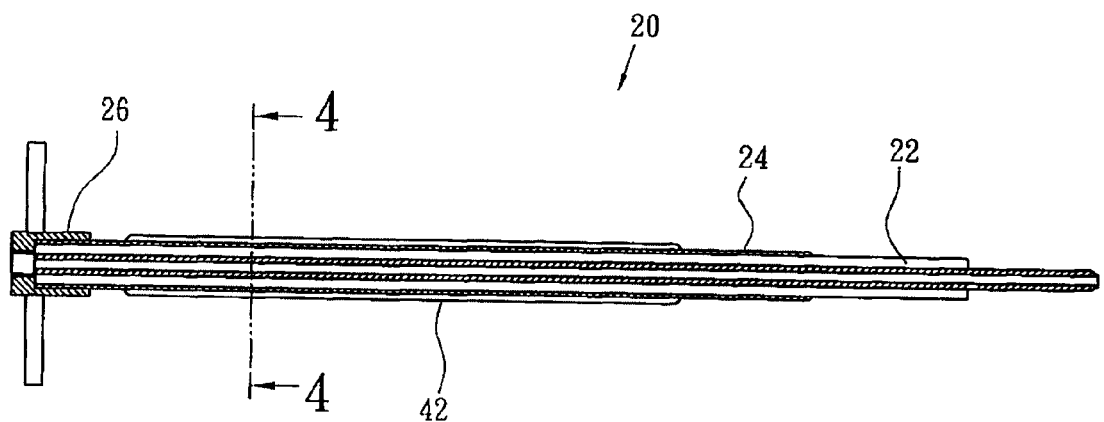
FIG. 3 is a cross-sectional view of the dilatation set shown in FIG. 1.
Figure 4:
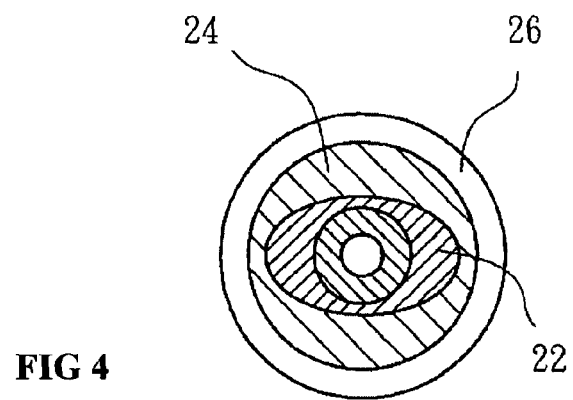
FIG. 4 is a cross-sectional view of the dilatation set taken along a line 4-4 in FIG. 3.
Figure 5:
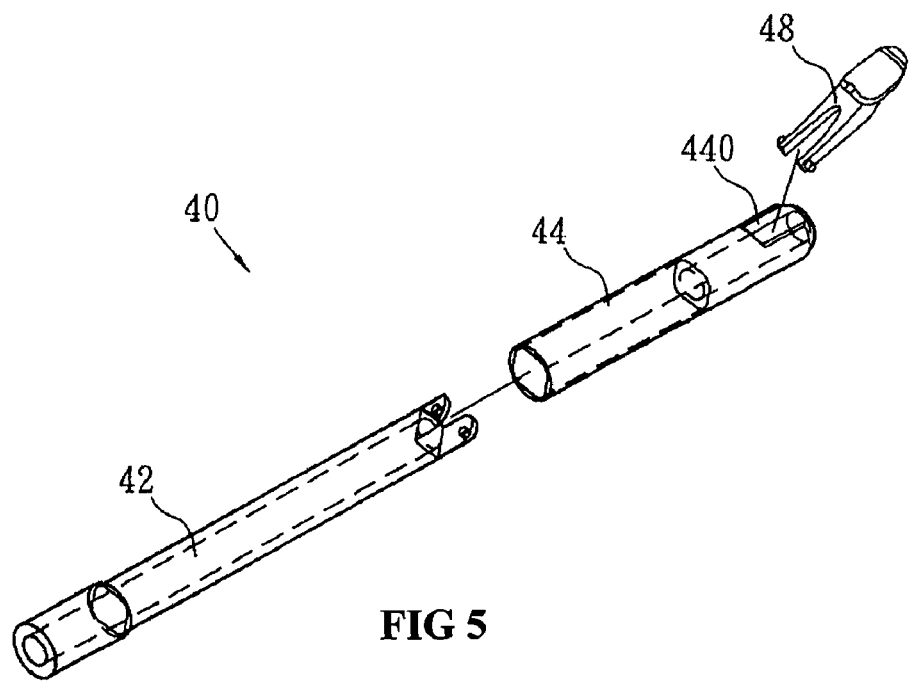
FIG. 5 is an exploded view of a guiding set of the apparatus.
Figure 6:
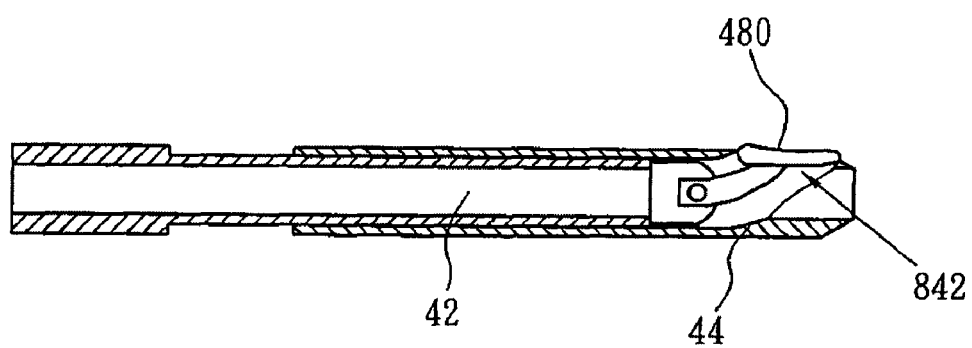
FIG. 6 is a cross-sectional view of the guiding set shown in FIG. 5.

Referring to FIGS. 5 and 6, the guiding set 40 includes a first guiding tube 42 and a second guiding tube 44 provided around the first guiding tube 42. The second guiding tube 44 includes a rectangular axial hole defined therein and a guiding hole 440 defined therein near an end. The guiding hole 440 is in communication with the rectangular axial hole of the second guiding tube 44. The interior of the first guiding tube 42 is in communication with the exterior of the second guiding tube 44 via the guiding hole 440.

In use, the guiding set 40 is inserted into the gap between the vertebral bodies along the second dilatation barrel 24. Then, the first guiding tube 42 is removed but the second guiding tube 44 is left in the gap between the vertebral bodies so that the guiding hole 440 is placed in the extended gap between the two vertebral bodies.

To prevent the edge of the guiding hole 440 from cutting any human organ, a support piece 48 is placed in the guiding hole 440. The edge of the support piece 48 is in contact with the edge of the guiding hole 440. The support piece 48 is formed with an arched face 480 that is flush with the periphery of the second guiding tube 44 near the guiding hole 440. Thus, the edge of the guiding hole 440 is prevented from cutting any human organs. After the second guiding tube 44 is set in position, the support piece 48 is removed.

Referring to FIGS. 7 and 8, the insert set 60 includes a leading rod 61, a push rod 62, a hammer sleeve 63, a block ring 64, a flexible element 65 and a helical spring 66. The leading rod 61 is movably inserted in the second guiding tube 44. The push rod 62 is a hollow element formed with a transversely extensive portion. The transversely extensive portion of the push rod 62 is pivotally connected to the leading rod 61. A thread formed on an internal side of the hollow hammer sleeve 63 is engaged with a thread formed on an external side of the leading rod 61. The block ring 64 is placed in the hammer sleeve 63 and includes a hexagonal hole 640 defined in a reduced end thereof. The reduced end of the block ring 64 is inserted through the hammer sleeve 63. The flexible element 65 extends through the leading rod 61 and the push rod 62. The flexible element 65 includes a first end fit in the block ring 64 and a second end located outside the push rod 62. The helical spring 66 is compressed between the block ring 64 and the leading rod 61 for biasing the block ring 64.

Referring to FIGS. 7, 9 and 10, the cage 80 includes an arced portion for insertion through the guiding hole 440. The cage 80 further includes a pocket defined between two prongs formed at an end thereof. A block 800 is formed at the end of the cage 80 and placed in the pocket. A rotating ring 84 includes a screw hole 840 defined therein in a radial manner and a groove 842 defined therein along the periphery thereof. The groove 842 includes two closed ends. The rotating ring 84 is placed in the pocket defined in the cage 80. A pin 82 is fit in the rotating ring 84 via the prongs of the cage 80 to rotationally connect the rotating ring 84 to the cage 80. The block 800 is placed in the groove 842. An end of the flexible element 65 is driven in the screw hole 840 to connect the flexible element 65 to the rotating ring 84 so that the flexible element 65 is pivotally connected to the cage 80 via the rotating ring 84. The closed ends of the groove 842 can contact the block 800 to limit the swing of the cage 80 relative to the flexible element 65. By the helical spring 66, the cage 80 is biased against the push rod 62 via the block ring 64 and flexible element 65.

In operation, the cage 80 is connected to the flexible element 65 and placed against the push rod 62. The leading rod 61, the push rod 62 and the cage 80 are inserted in the second guiding tune 44. Then, by the leading rod 61 and the push rod 62, the cage 80 is pushed into the expanded gap between the vertebral bodies from the second guiding tube 44 via the arched face of the guiding hole 440. The cage 80 pivots gradually to reach a predetermined angle.

If necessary, an operator can pull the flexible element 65 via the block ring 64 to position the cage 80 precisely. After the cage 80 is positioned as shown in FIG. 11, the operator can release the cage 80. To this end, an Allen key is used to turn the block ring 64 and rotate the flexible element 65 to release the cage 80. Then, the insertion is finished by pulling out the insert set 60 and the second guiding tube 44 sequentially.

The apparatus of the present invention exhibits at least three advantages. At first, the gap between two vertebral bodies is expanded by the first dilatation barrel 22 to reduce the surgery time. Secondly, the cage 80 is moved in the gap between the vertebral bodies along an arched path and the angle thereof is automatically changed by the arched guiding hole 440 defined in the second guiding tube 44. Thirdly, the cage 80 is positioned precisely by the flexible element 65 inserted in the hollow insert set 60.

Although the invention has been explained in relation to its preferred embodiment, it is not used to limit the invention. It is to be understood that many other possible modifications and variations can be made by those skilled in the art without departing from the spirit and scope of the invention as hereinafter claimed.

What is claimed is:

1. An apparatus for inserting an intervertebral fusion cage, including:
   a dilatation set including;
      a first dilatation barrel formed with a circular internal cross-sectional configuration and an elliptic external cross-sectional configuration; and
      a second dilatation barrel provided around the first dilation barrel, and formed with an elliptic internal cross-sectional configuration and a circular external cross-sectional configuration;
   a guiding set including:
      a first guiding tube provided around the second dilatation barrel; and
      a second guiding tube provided around the first guiding tube, and formed with a radial guiding hole defined therein and a smooth face formed thereon in the guiding hole;
   an insert set including:
      a leading rod inserted in the second guiding tube;
      a push rod pivotally connected to the leading rod and movably inserted in the second guiding tube;
      a tubular hammer sleeve connected to the leading rod;
      a block ring inserted in the hammer sleeve;

a spring compressed between the block ring and the leading rod; and a flexible element connected to the block ring; and an intervertebral fusion cage connected to the flexible element, inserted in the second guiding tube, pushed against the push rod, and formed with an arced face movable out of the second guiding tube via the guiding hole along the smooth face and adjustable to a predetermined angle.

2. An apparatus for inserting an intervertebral fusion cage as claimed in claim 1, wherein the second guiding tube includes an internal cross-sectional configuration corresponding to an external configuration of the intervertebral fusion cage.

3. An apparatus for inserting an intervertebral fusion cage as claimed in claim 2, wherein the internal cross-sectional configuration of the second tube is rectangular.

4. An apparatus for inserting an intervertebral fusion cage as claimed in claim 1, wherein the guiding set includes a supporting piece fit in the guiding hole.

5. An apparatus for inserting an intervertebral fusion cage as claimed in claim 1, including a rotating ring connected to the flexible element, rotationally located in the intervertebral fusion cage, and formed with a groove, wherein the intervertebral fusion cage includes a block located in the groove to limit the swing of the intervertebral fusion cage relative to the flexible element.

6. An apparatus for inserting an intervertebral fusion cage as claimed in claim 1, wherein the dilatation set includes a handle including a non-circular aperture corresponding to the first dilatation barrel, wherein the first dilatation barrel is non-rotationally but movably inserted through the non-circular aperture of the handle.

\* \* \* \* \*